United States Patent [19]

Koga et al.

[11] Patent Number: 5,660,838
[45] Date of Patent: Aug. 26, 1997

[54] SKIN PREPARATIONS FOR EXTERNAL USE

[75] Inventors: Kunimasa Koga, Osaka; Takumi Kobayashi; Shigeaki Fujikawa, both of Kanagawa-ken; Masako Sawada, Osaka, all of Japan

[73] Assignee: Suntory Limited, Osaka, Japan

[21] Appl. No.: 394,201

[22] Filed: Feb. 24, 1995

Related U.S. Application Data

[63] Continuation of Ser. No. 8,873, Jan. 25, 1993, abandoned, which is a continuation of Ser. No. 708,202, May 31, 1991, abandoned.

[30] Foreign Application Priority Data

May 31, 1990 [JP] Japan ................... 2-142845

[51] Int. Cl.$^6$ ................... A61K 7/06; A61K 7/48
[52] U.S. Cl. ................... 424/401; 424/70.13; 514/873
[58] Field of Search ................... 424/401, 493, 424/70.13; 514/53, 873, 847; 435/100; 536/123.1, 123.13

[56] References Cited

U.S. PATENT DOCUMENTS

| | | | |
|---|---|---|---|
| 4,364,837 | 12/1982 | Pader | 424/70.11 |
| 4,761,401 | 8/1988 | Couchman et al. | 514/880 |
| 4,818,751 | 4/1989 | Ibe | 514/54 |

FOREIGN PATENT DOCUMENTS

| | | |
|---|---|---|
| 01055150 | 3/1989 | Japan. |
| 0252280 | 10/1989 | Japan. |
| 0252281 | 10/1989 | Japan. |
| 02100694 | 4/1990 | Japan. |
| 02119790 | 5/1990 | Japan. |

OTHER PUBLICATIONS

Patent Abstracts of Japan, vol. 9, No. 188 (C–295) [1911], 3rd Aug. 1985; & JP-A60 58 070 (Rikagaku Kenkyusho Apr. 4, 1985).

*Primary Examiner*—John C. Bleutge
*Assistant Examiner*—Robert H. Harrison
*Attorney, Agent, or Firm*—Cushman Darby & Cushman IP Group of Pillsbury Madison & Sutro LLP

[57] ABSTRACT

Xylobiose-containing skin preparations for external use are disclosed. Skin preparations for external use into which xylobiose may be incorporated include cosmetics such as clear lotions, milky lotions, packs and lip treatments, drugs or quasidrugs such as ointments and cataplasms, hair-care products such as rinses and hair conditions, and detergents such as hair shampoos and body shampoos. Xylobiose is typically contained in an amount of 0.0001–20 wt %, preferably 0.1–10 wt %, of the total amount of the skin preparation on a dry solids basis. The incorporation of xylobiose is effective not only in preventing the occurrence of stickiness, color change and malodor in the skin preparations but also in providing enhanced moisture retention and reducing excessive roughness and dryness of the skin and hair.

3 Claims, No Drawings

SKIN PREPARATIONS FOR EXTERNAL USE

This is a continuation of application Ser. No. 08/008,873, filed on Jan. 25, 1993, which was abandoned upon the filing hereof which was a continuation of application Ser. No. 07/708,202, filed May 31, 1991, abandoned.

BACKGROUND OF THE INVENTION

This invention relates to skin preparations for external use that are effective not only in reducing excessive roughness and dryness of the skin to impart a natural moistness and luster but also in reducing excessive roughness and dryness of the hair to give a natural oiliness.

One of the major objectives of applying cosmetics and other skin preparations for external use is to prevent and reduce excessive roughness and dryness of the skin. To this end, various humectants have been incorporated in skin preparations for external use. However, conventionally used humectants have their own problems. For example, polysaccharides tend to cause precipitation when used in alcoholic formulation; polyhydric alcohols and chondroitin sulfate cause stickiness or a slightly burning sensation when incorporated in large quantities; and amino acids such as DL-alanine sometimes cause coloration or malodor.

SUMMARY OF THE INVENTION

Under these circumstances, the present inventors conducted intensive studies in order to obtain skin preparations for external use that had good storage stability, that exhibited a high moisture retaining effect and that were free from the problems of stickiness, coloration and malodor. As a result, the present inventors found that xylobiose-containing skin preparations for external use satisfied these requirements and the present invention has been accomplished on the basis of this finding.

DETAILED DESCRIPTION OF THE INVENTION

The present invention is characterized by incorporation of xylobiose which results in solving the various problems encountered with the prior art skin preparations for external use.

Xylobiose used in the present invention is a disaccharide (mol. wt. 282) that, as shown below, comprises two molecules of xylose which is a pentose that are polymerzed via $\beta$-1,4 bond:

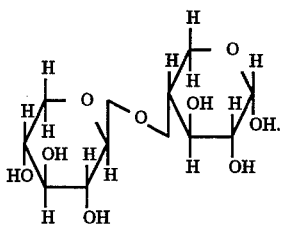

Xylose is the constituent of xylan which is a polysaccharide in plants and it has long been taken into the human body as a non-calorie saccharide. Xylan is a kind of hemicelluloses that have recently come to be recognized as useful edible vegetable fibers and it is known that xylan occurs extensively in the fibrous portions of cottonseeds, corns, malt and sugar canes.

Xylobiose as it occurs naturally is known to be contained in bamboo in very small amount and in a free state.

Plant-derived fibers such as celluloses and hemicelluloses are used as starting materials for the manufacture of foods and cosmetics. Noting oligosaccharides which are fibrous polysaccharides of shorter sugar chains, the present inventors previously developed efficient processes for preparing xylobiose which occurs naturally in only very small amounts (Japanese Laid-Open Patent Application Nos. 155095/1987, 242592/1986 and 100694/1990).

As a result of continued studies, the present inventors have found that xylobiose is useful as a component of skin preparations for external use and that it provides preparations with the ability to retain moisture without causing any stickiness and that it is stable without causing coloration or malodor.

The skin preparations for external use that can benefit from the incorporation of xylobiose in accordance with the present invention include cosmetics, drugs, quasidrugs and other products that are to be used on or applied to the skin or hair. Such skin preparations can be formulated in widely varying dosage forms including aqueous solutions, solubilizable systems, emulsions and water/oil bilayer systems. Specific examples of the skin preparations include cosmetics such as moisture creams, clear lotions, milky lotions, packs and lip treatments, drugs or quasidrugs such as ointments and cataplasms, hair-care products such as hair treatments, rinses and hair conditioners, and detergents such as hair shampoos and body shampoos.

The amount in which xylobiose is to be incorporated in the preparation of the present invention is determined by its efficacy and economy. Having no toxicity to humans, xylobiose can be incorporated in any amount without causing the toxicity problem. However, in consideration of the need to achieve the intended effect and of the fact that increasing the xylobiose content beyond a certain level will not contribute to any corresponding enhancement of the efficacy, xylobiose may usually be incorporated in an amount of 0.0001–20 wt %, preferably 0.1–10 wt %, of the total amount of the skin preparation on a dry solids basis.

Xylobiose can be used in the present invention as a xylobiose composition that is prepared by saccharifying xylan with a xylobiose generating enzyme. The thus prepared xylobiose composition contains xylan saccharified products other than xylobiose such as xylose and xylotriose. These materials will in no way impair the moisture retaining capability of xylobiose but the xylobiose content of said composition is preferably at least 20% (all percentages that appear hereinafter are on a weight basis), more preferably at least 50%.

As a xylobiose generating enzyme, there can be employed a commercially available enzyme, for example, derive from *Trichoderma viride*, *Aspergillus niger*, *Humicola lanuginosa*, *Chaetomium graeile*, or *Bacillus Pumilus*.

The skin preparations for external use of the present invention may contain known components in ordinary amounts. The components that can be used in addition to xylobiose in the skin preparation of the present invention are described below with reference to cosmetics.

Bases that can be used in cosmetics as an example of the skin preparations of the present invention may be selected from a class of bases that are commonly incorporated as cosmetic components and include the following: animal and plant derived materials such as almond oil, avocado oil, olive oil, turtle oil, bees wax, squalene, lanolin and castor oil; mineral materials such as liquid paraffin, ceresin, paraffin wax, microcrystalline wax, vaseline, candelilla wax, carnauba wax and Japan wax; fatty acids such as palmitic acid and stearic acid; alcohols such as ethanol; higher alcohols such as cetanol, stearyl alcohol, lanolin alcohol, octyl dodecanol and polyvinyl alcohol; esters such as isopropyl myristate, butyl stearate, acetoglyceride, acetylated lanolin, glycerin monostearate, polyoxyethylene monoleate ester, polyethylene glycol monostearic acid ester, and ethyl monooleate; amines such as triethanolamine; ethers such as polyoxyethylene cetyl ether; and silicone oils.

Besides these bases, the following components can be used as required: surfactants such as Spans, Tweens, sugar esters and polyhydric alcoholic esters; mucilages such as acasia gum, tragacanth gum, karaya gum, quince gum, pectin, methyl cellulose, hydroxymethyl propyl cellulose and carboxymethyl cellulose sodium; humectants such as glycerin, propylene glycol, sorbitol, diethylene glycol monoethyl ether and citric acid; extracts from various animals and plants; vitamins; amino acids; activators such as agents to enhance blood circulation; various enzymes; anti-inflammatories; saccharides; pigments; biocides or preservatives; antioxidants; and perfumes.

To evaluate safety for humans and animals, cosmetics incorporating xylobiose according to the present invention were subjected to tests on percutaneous acute toxicity and skin irritation and nothing abnormal was found on the skin.

An example of the process for preparing xylobiose that can be used in the skin preparation of the present invention is described below.

REFERENCE EXAMPLE
(for the Preparation of Xylobiose)

A plant-derived xylan as a starting material was saccharified in an aqueous solution with a xylobiose generating enzyme at 40° C. for 19 h at a pH of 7.0. After filtration, the resulting saccharified solution was treated with activated carbon and concentrated sulfuric acid at 60° C. for 2 h at a pH of 2.0 to effect discoloration and deprotenization. Diatomaceous earth was added to the treated product and the mixture was filtered with a filter press. Subsequently, the filtrate was concentrated by reverse osmosis to obtain a concentrated saccharified solution. This solution was desalted by successive passage through a cation-exchange resin, an anion-exchange resin and a mixed-bed resin. Activated carbon was added to the treated solution, which was held at 25° C. for 30 min at a pH of 4–6.5 to effect discoloration. Diatomaceous earth was added to the obtained solution, which was then filtered with a filter press. The filtrate was concentrated under vacuum at 60° C. for 4 h to prepare a xylobiose composition.

The xylan saccharified product thus obtained contained xylobiose as the main ingredient, with xylose, xylotriose and other substances being present in only negligible amounts. The saccharified products concomitant to xylobiose are in no way detrimental to the moisture retaining capability of xylobiose but the content of xylobiose in the xylobiose composition is desirably at least 20%. If necessary, the concentration of xylobiose can be enhanced with the aid of a reverse osmotic membrane.

The xylobiose composition thus obtained was treated with a reverse osmotic membrane to increase the xylobiose content to at least 95%.

The following experimental examples and working examples are provided for the purpose of further illustrating the present invention.

EXPERIMENTAL EXAMPLE 1

Measurement of Moisture Retaining Capability of Xylobiose in Terms of the Rate of Water Eveporation (on Aqueous Solutions)

Various humectants were dissolved in water to make 50% aqueous solutions and their hygroscopic property at high humidity as well as their ability to retain water at low humidity were evaluated.

Material under test:
  Xylobiose composition (containing at least 95% xylobiose)
Comparative humectants:
  Sorbitol
  1,3-butylene glycol
  Propylene glycol
  Glycerin
Testing environment:
  Condition A . . . 35° C. and 95% r.h.
    (this condition was created in a thermostatic chamber at 35° C. by leaving in it a desiccator that contained a saturated aqueous solution of sodium monohydrogen phosphate.)
  Condition B . . . 35° C. and 40% r.h.
    (this condition was created in a thermostatic chamber at 35° C. by leaving in it a desiccator that contained a solution of calcium chloride.)
Method of measurement:
  Each of the material under test and the comparative humectants was dissolved in water to make a 50% aqueous solution; 2 g of the solution was left under either condition A or B for 24 h and 70 h to measure the resulting changes in weight.
Results of measurement:
  (1) High-humidity condition (A)
    Under the high-humidity condition, all samples absorbed water but in varying degrees: after 70 h, the material under test (xylobiose) experienced a weight change of +6.1% whereas the respective values for the comparative humectants were +27.6% (glycerin), +26.5% (propylene glycol), +19.8% (1,3-butylene glycol) and +10.9% (sorbitol). It was therefore clear that Xylobiose was less prone to absorb moisture than the comparative humectants under high humidity (see Table 1).
  (2) Low-humidity condition (B)
    Under the low-humidity condition, all samples experienced evaporation but in varying degrees: after 70 h, the material under test (xylobiose) experienced a weight change of –42.4% whereas the respective values for the comparative humectants were –39.9% (glycerin), –45.7% (propylene glycol), –44.3% (1,3-butylene glycol) and –42.5% (sorbitol). Obviously, xylobiose was less effective than glycerin in retaining moisture at low humidity but it was more effective than the other comparative humectants (see Table 2).

Discussion:
On the basis of the results described above, it can be concluded that under high-humidity conditions such as in summer, xylobiose absorbs less moisture and hence is less sticky whereas under low-humidity conditions, xylobiose prevents evaporation of water from the skin. Hence, xylobiose has ideal properties as a humectant to be incorporated in cosmetics.

TABLE 1

Weight changes at 95% r. h. and 35° C.

| Test material | Weight, g (parenthesized figures refer to percent weight change) | | |
| --- | --- | --- | --- |
| | 0 h | 24 h | 70 h |
| Xylobiose composition | 2.00 | 2.01486 (0.743) | 2.12140 (6.07) |
| Sorbitol | 2.00 | 2.06613 (3.31) | 2.21764 (10.88) |
| 1,3-Butylene glycol | 2.00 | 2.12273 (6.14) | 2.39539 (19.77) |

TABLE 1-continued

Weight changes at 95% r. h. and 35° C.

| Test material | Weight, g (parenthesized figures refer to percent weight change) | | |
|---|---|---|---|
| | 0 h | 24 h | 70 h |
| Propylene glycol | 2.00 | 2.18533 (9.27) | 2.53065 (26.53) |
| Glycerin | 2.00 | 2.19537 (9.77) | 2.55151 (27.58) |

TABLE 2

Weight changes at 40% r. h. and 35° C.

| Test material | Weight, g (parenthesized figures refer to percent weight change) | | |
|---|---|---|---|
| | 0 h | 24 h | 70 h |
| Xylobiose composition | 2.00 | 1.31634 (−34.18) | 1.15121 (−42.44) |
| Sorbitol | 2.00 | 1.42623 (−28.69) | 1.14923 (−42.54) |
| 1,3-Butylene glycol | 2.00 | 1.49765 (−25.12) | 1.11389 (−44.31) |
| Propylene glycol | 2.00 | 1.61146 (−19.43) | 1.08590 (−45.71) |
| Glycerin | 2.00 | 1.64412 (−17.79) | 1.20282 (−39.86) |

EXPERIMENTAL EXAMPLE 2

Measurement of Moisture Retaining Capability in Terms of the Rate of Water Evaporation (on Moisture Creams)

Material under test:

Xylobiose composition (containing at least 954 xylobiose)

Comparative humectants:
  Sorbitol
  1,3-butylene glycol
  Propylene glycol
  Glycerin Testing environment:
  Condition A . . . 25° C. and 38% r.h.
  (this condition was created in a thermostatic chamber at 25° C. by leaving in it a desiccator that contained a solution of calcium chloride.)
  Condition B . . . 35° C. and 40% r.h.
  (this condition was created in a thermostatic chamber at 35° C. by leaving in it a desiccator that contained a solution of calcium chloride.)

Moisture cream:

Commercial product

Method of measurement:

To each of the moisture creams provided, the material under test or the comparative humectants were added, each one in an amount of 5%, the creams were then left to stand under condition A or B and their weight was measured at 24, 48 and 72 h to determine the changes from the 0-h value.

As a control, an O/W cream containing no humectant was provided.

Results:

(1) Comparison between O/W cream containing the material under test and the control The weight change that occurred in the O/W cream containing the material under test was −3.6% under condition A and −16.8% under condition B after 72 h. In comparison, the control cream experienced weight changes of −13.1% and −31.8% under conditions A and B, respectively. It was therefore apparent that the moisture retention of cream was enhanced by addition of the material under test (see Tables 3 and 4).

(2) Comparison between the material under test and the comparative humectants

After 72 h standing under condition A, the O/W cream containing the material under test experienced a weight change of −3.6%, which indicates the better moisture retaining quality of xylobiose than 1,3-butylene glycol (−3.6%), glycerin (−3.8%), propylene glycol (−3.9%) and sorbitol (−3.9%) (see Table 3). Similar results were obtained after standing for 24 h and 48 h.

After 72 h standing under condition B, the O/W cream containing the material under test experienced a weight change of −16.8%, which indicates the better moisture retaining quality of xylobiose than 1,3-butylene glycol (−16.9%), glycerin (−17.4%), propylene glycol (−18.6%) and sorbitol (−17.9%) (see Table 4).

TABLE 3

Weight changes at 38% r.h. and 25° C.

| Test material | Cream weight (g) | Total weight (container + cream) g, (parenthesized figures refer to percent weight change) | | | |
|---|---|---|---|---|---|
| | | 0 h | 24 h | 48 h | 72 h |
| Xylobiose composition | 10.41 | 16.8051 | 16.5923(−2.04) | 16.5121(−2.81) | 16.4323(−3.58) |
| Sorbitol | 10.04 | 16.4089 | 16.1593(−2.49) | 16.0846(−3.23) | 16.0146(−3.93) |
| 1,3-Butylene glycol | 10.04 | 16.3207 | 16.0881(−2.32) | 16.0193(−3.00) | 15.9558(−3.63) |
| Propylene glycol | 9.96 | 16.3260 | 16.082(−2.45) | 16.0040(−3.23) | 15.9430(−3.85) |
| Glycerin | 10.60 | 16.9012 | 16.6313(−2.55) | 16.5574(−3.24) | 16.5020(−3.77) |
| Control (no humectant added) | 7.10 | 11.1514 | 10.8811(−3.81) | 10.4824(−9.42) | 10.2237(−13.07) |

TABLE 4

Weight changes at 40% r.h. and 35° C.

| Test material | Cream weight (g) | Total weight (container + cream) g, (parenthesized figures refer to percent weight change) | | | |
|---|---|---|---|---|---|
| | | 0 h | 24 h | 48 h | 72 h |
| Xylobiose composition | 10.24 | 16.6145 | 15.8604(−7.36) | 15.3467(−12.38) | 14.8967(−16.78) |
| Sorbitol | 10.33 | 16.7210 | 16.0532(−6.46) | 15.5193(−11.63) | 14.8703(−17.92) |
| 1,3-Butylene glycol | 10.24 | 16.4862 | 15.8411(−6.30) | 15.3356(−11.24) | 14.7528(−16.93) |
| Propylene glycol | 9.86 | 16.3127 | 15.5515(−7.72) | 14.9856(−13.46) | 14.4817(−18.57) |
| Glycerin | 10.26 | 16.5508 | 15.8313(−7.01) | 15.3524(−11.68) | 14.7690(−17.37) |
| Control (no humectant added) | 5.88 | 9.8746 | 8.9057(−16.48) | 8.3494(−25.94) | 8.0032(−31.83) |

Discussion:

On the basis of the results described above, it can be concluded that the O/W cream containing xylobiose is comparable to or more effective than the O/W creams containing other humectants as regards moisture retention.

The moisture cream containing Xylobiose that was prepared in Experimental Example 2 was actually applied to the skin; it had high affinity for the skin, produced a refreshing feel, had no stickiness, and hence was found to be satisfactory from an organoleptic viewpoint.

The following working examples are provided for describing the formulations of various products in accordance with the present invention and the processes for producing them.

EXAMPLE 1

Clear Lotion

A xylobiose-containing clear lotion was prepared to the recipe described below:

| Component | Amount (%) |
|---|---|
| Xylobiose composition (containing at least 95% xylobiose) | 1.0 |
| Propylene glycol | 1.0 |
| Citric acid | 0.2 |
| 95% Ethanol | 10.0 |
| Perfume | q.s. |
| POE lauryl ether | 0.5 |
| Distilled water | bal. |

When actually applied to the skin, the lotion had good affinity for the skin, produced a refreshing feel, had no stickiness and hence was found to be satisfactory from an organoleptic viewpoint.

EXAMPLE 2

Milky Lotion

A xylobiose-containing milky lotion was prepared to the recipe described below. When actually applied to the skin, the lotion had good affinity for the skin, produced a refreshing feel, had no stickiness and hence was found to be satisfactory from an organoleptic viewpoint.

| Component | | Amount (%) |
|---|---|---|
| Oily ingredients: | stearic acid | 2.0 |
| | cetanol | 1.5 |

-continued

| Component | | Amount (%) |
|---|---|---|
| | Vaseline | 3.0 |
| | lanolin alcohol | 2.0 |
| | liquid paraffin | 10.0 |
| Emulsifier: | polyoxyethylene monooleic acid ester | 2.0 |
| Perfume | | 0.5 |
| Antiseptic and antioxidant | | q.s. |
| Humectant: | xylobiose composition (containing at least 95% xylobiose) | 8.0 |
| Alkali: | triethanolamine | 1.0 |
| Purified water | | 70.0 |

EXAMPLE 3

Nourishing Cream

A xylobiose-containing nourishing cream was prepared to the recipe described below. When actually applied to the skin, the cream had good affinity for the skin, produced a refreshing feel, had no stickiness and hence was found to be satisfactory from an organoleptic viewpoint.

| Component | Amount (%) |
|---|---|
| Stearic acid | 2.0 |
| Stearyl alcohol | 7.0 |
| Reduced lanolin | 2.0 |
| Squalane | 5.0 |
| Octyl dodecanol | 6.0 |
| POE (25 mol %) cetyl ether | 3.0 |
| Glycerin monostearate | 2.0 |
| Antiseptic | q.s. |
| Perfume | q.s. |
| Propylene glycol | 5.0 |
| Xylobiose composition (containing at least 95% xylobiose) | 1.0 |
| Distilled water | bal. |

EXAMPLE 4

Pack

A xylobiose-containing pack was prepared to the recipe described below. When actually applied to the skin, the pack had good affinity for the skin, produced a refreshing feel, had no stickiness and hence was found to be satisfactory from an organoleptic viewpoint.

| Component | Amount (%) |
| --- | --- |
| Film forming agent: polyvinyl alcohol | 15.0 |
| Thickener: sodium carboxymethyl cellulone | 5.0 |
| Humectant: xylobiose-containing composition (containing at least 95% xylobiose) | 3.0 |
| Ethanol | 10.0 |
| Perfume | 0.5 |
| Antiseptic and antioxidant | q.s. |
| Purified water | 66.5 |

EXAMPLE 5

Lip Treatment

A xylobiose-containing lip treatment was prepared to the recipe described below. When actually applied to the skin, the treatment had good affinity for the skin, produced a refreshing feel, had no stickiness and hence was found to be satisfactory from an organoleptic viewpoint.

| Component | Amount % |
| --- | --- |
| Candelilla wax | 9.0 |
| Solid paraffin | 8.0 |
| Beeswax | 5.0 |
| Carnauba wax | 5.0 |
| Lanolin | 11.0 |
| Castor oil | bal. |
| Xylobiose-containing composition (containing at least 95% xylobiose) | 0.1 |
| Isopropyl myristate | 10.0 |
| Perfume | q.s. |
| Antioxidant | q.s. |

EXAMPLE 6

Ointment

A xylobiose-containing ointment was prepared to the recipe described below. When actually applied to the skin, ointment had good affinity for the skin, produced a refreshing feel, had no stickiness and hence was found to be satisfactory from an organoleptic viewpoint.

| Component | Amount % |
| --- | --- |
| Stearyl alcohol | 18.0 |
| Japan wax | 20.0 |
| Xylobiose composition (containing at least 95% xylobiose) | 0.5 |
| Ethyl monooleate | 0.5 |
| Vaseline | 40.0 |
| Purified water | bal. |

EXAMPLE 7

Hair Shampoo

A xylobiose-containing hair shampoo was prepared to the recipe described below. When actually applied to the hair, a natural oiliness was imparted both to the skin and hair and the results were satisfactory from an organoleptic viewpoint.

| Component | Amount % |
| --- | --- |
| Hydroxymethylpropyl cellulose | 0.2 |
| Water | 56.0 |
| Amisoft CT-12 (30% aq. sol.) | 29.0 |
| Amizol CDE | 4.5 |
| Sodium salt | 0.4 |
| Xylobiose composition (containing at least 95% xylobiose) | 8.9 |
| Polyethylene glycol monostearate | 1.0 |

As is clear from the foregoing description, the skin preparations for external use that incorporate xylobiose in accordance with the present invention are free from the problems of stickiness, color change and malodor and prove very effective in moisture retention and in reducing excessive roughness and dryness of the skin and hair.

What is claimed is:

1. A method for reducing the roughness and dryness of human skin or hair which comprises applying thereto, in an amount sufficient to reduce roughness and dryness of human skin or hair, a composition for external application to human skin or hair comprising a xylobiose composition that is prepared by saccharifying xylan with a xylobiose generating enzyme and a carrier conventionally accepted for a preparation for external application to human skin or hair, said xylobiose composition containing at least 50% by weight of xylobiose, and said composition for external application containing xylobiose in an amount of from 0.1 to 10% by weight of the total amount of said composition for external application.

2. A method according to claim 1 wherein said composition for external application is in the form selected from the group consisting of a drug, quasidrug, cosmetic, haircare product and detergent.

3. A method according to claim 1 wherein said composition for external application is in the form selected from the group consisting of a clear lotion, milky lotion, cream, pack, lip treatment, ointment, cataplasm, hair treatment, hair rinse, hair conditioner and shampoo.

* * * * *